United States Patent [19]

Bertelli

[11] 4,156,737
[45] May 29, 1979

[54] p-AMINOMETHYL-BENZENE-SULFONAMIDE DERIVATIVES, PROCESS FOR THEIR PREPARATION AND APPLICATIONS THEREOF

[75] Inventor: Aldo Bertelli, Milan, Italy

[73] Assignee: Seuref A.G., Vaduz, Liechtenstein

[21] Appl. No.: 895,853

[22] Filed: Apr. 12, 1978

[30] Foreign Application Priority Data

Apr. 14, 1977 [FR] France .................. 77 11222

[51] Int. Cl.² .................. A01N 9/00; C07F 3/06; C07F 5/06; C07F 1/08; C07F 1/10
[52] U.S. Cl. .................. 424/287; 260/429.2; 260/429.9; 260/430; 260/438.1; 260/448 R; 424/289; 424/290; 424/294
[58] Field of Search ............. 260/430, 438.1, 429.9, 260/448 R, 429.2; 424/1, 287, 289, 290, 294

[56] References Cited

U.S. PATENT DOCUMENTS

| 2,536,095 | 1/1951 | Rasenzweig et al. | 260/429.9 X |
| 2,901,475 | 8/1959 | Rudner et al. | 260/430 X |
| 2,993,829 | 7/1961 | Lemin | 424/294 |
| 3,192,107 | 6/1965 | Whitmoyer et al. | 424/228 |
| 3,497,599 | 2/1970 | Nachod | 424/321 |
| 3,541,051 | 11/1970 | Hirata et al. | 424/321 X |

Primary Examiner—Helen M. S. Sneed
Attorney, Agent, or Firm—Young & Thompson

[57] ABSTRACT

This invention relates to p-aminomethyl-benzene-sulfonamide derivatives having the formula:

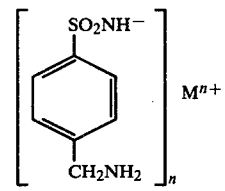

in which M is an ion of a metal atom selected from silver, zinc, aluminum, copper and cerium, and n is an integer from 1 to 4.

Said compounds have typically an anti-bacterial activity, and also a healing and protective effect on skin burns.

2 Claims, No Drawings

P-AMINOMETHYL-BENZENE-SULFONAMIDE DERIVATIVES, PROCESS FOR THEIR PREPARATION AND APPLICATIONS THEREOF

This invention relates to new p-aminomethyl benzene sulfonamide derivatives having anti-bacterial and healing chemotherapeutic activities, having particular therapeutic usefulness in human medicine for the treatment of infected skin lesions and of burns.

Said compounds have the general formula:

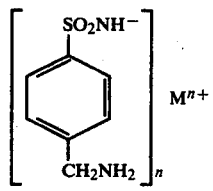
(I)

in which M is an ion from a metal atom selected from silver, zinc, aluminum, copper and cerium, and n is an integer from 1 to 4.

The new compounds are p-aminomethyl-benzene-sulfonamide derivatives converted to the salt form with silver (Ag), zinc (Zn), aluminum (Al), copper (Cu) and cerium (Ce) ions.

This invention relates also to a process for the preparation of compounds having the above formula (I), comprising converting p-aminomethyl-benzene-sulfonamide to the salt form with a salt of a metal selected from silver, zinc, aluminum, copper and cerium.

Conversion to the salt form is preferably effected in aqueous medium, with stirring and in the presence of sodium bicarbonate. Salts which are useful for the reaction are typically chlorides and nitrates.

The compounds of the formula (I) are recovered by low temperature filtration.

The following non-limiting Examples are given to illustrate the preparation of compounds of this invention.

EXAMPLE 1

Preparation of p-aminomethyl-benzene-sulfonamide, silver salt:

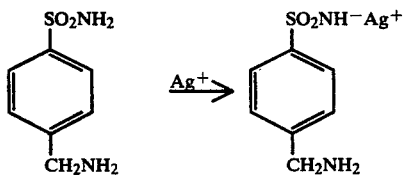

p-Aminomethyl-benzene-sulfonamide (18.6 g) is dissolved in distilled water. Sodium bicarbonate (10 g) is then added, followed by silver nitrate (17 g) dissolved in the smallest possible amount of distilled water, with stirring. The resulting material is cooled and filtered through a Buchner funnel, to give a white amorphous product which is dried in vacuo at 60° C. in an oven. The product is stored in the absence of light. Molecular weight 292.9. - for formula $C_7H_9N_2SO_2Ag$.

EXAMPLE 2

Preparation of p-aminomethyl-benzene-sulfonamide, zinc salt:

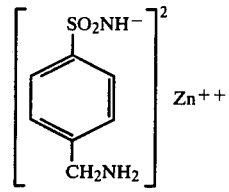

p-Aminomethyl-benzene-sulfonamide (18.6 g) is dissolved in distilled water (50 ml). Sodium bicarbonate (10 g) is then added thereto, followed by anhydrous $ZnCl_2$ (10 g) dissolved in the smallest possible amount of distilled water, with stirring.

The material is allowed to rest at a temperature of 5° C. for 24 hours, after which the resulting product is filtered off. The product is obtained as a non-hygroscopic stable white powder.

EXAMPLES 3–5

The aluminum, copper and cerium salts of p-aminomethylbenzene-sulfonamide are prepared in like manner and under the same experimental conditions.

The results of toxicological and pharmacological tests reported hereinafter provide evidence that the compounds of the formula (I) exhibit an antibacterial action against germs which, usually, infect skin lesions and burns, and also that they have a favourable action on the healing (cicatrization) process.

Thus, this invention includes also within its scope a therapeutic composition having in particular the aforesaid activities, comprising, as active ingredient, a p-aminomethylbenzene-sulfonamide derivative converted to the salt form with silver, zinc, aluminum, copper or cerium.

The active ingredient is generally combined with a therapeutically administrable carrier.

The results of a toxicological and pharmacological investigation conducted for illustrative purposes on the silver and zinc salts are given below.

Toxicological Investigation

The products of Examples 1 and 2 have very low toxicity.

Thus, by the intraperitoneal route, the $LD_{50}$ in mice was found to be 55 mg/kg and 80 mg/kg, respectively.

After topical application, both on the skin of rabbits and on the skin of rats, the products of Examples 1 and 2 were equally well tolerated and free from any apparent toxicity.

High dosages of said products, suspended in suitable excipients, could be applied without any evidence of toxic symptons.

Application of said products was effected on the skin of animals both after depilation and after depilation and abrasion, so as to obtain continuous skin lesions.

On evaluation of the chronic toxicity of the test derivatives, it was found that none of the treated animals exhibited signs of toxicity or of intolerance related to the administration of the products, even on administration for forty-five consecutive days in rats and 30 consecutive days in rabbits by application on depilated normal skin or on depilated skin submitted to a surface abrasion of a 10% and 20% suspension of the products at dosages varying between 250 mg/kg and 750 mg/kg.

In particular, no modification was found on examination of the weight increase, of the differential leucocyte count, of azotemia, of the transaminases and of urinary excretion.

Similarly, no modification was detected on anatomopathologic and physiological examinations conducted at the level of the main organs of the treated animals. In addition, the histological examination conducted on skin samples taken from the treated animals failed to disclose any modification of inflammatory or degenerative type due to treatment with the products of Examples 1 and 2.

Pharmacological Investigation

A. Anti-bacterial action

Various tests were used to determine the anti-bacterial activity of the products of Examples 1 and 2 with respect to p-aminomethyl-benzene-sulfonamide. Said tests were effected according to the agar dilutions on Mueller-Hinton medium. The inoculum is prepared by means of an automatic Multipoint Inoculation apparatus, with a 24 hrs broth culture diluted to 1/10.

The test materials are suspended in a Twin solution.

The following germ strains were used: E. coli 130; E. coli 3671; E. coli K 12; E. coli 334; Pseudomonas 66/5; Pseudomonas 630412; Pseudomonas Paffoni; Staphylococcus 209 P; Staphylococcus 153; Pseudomonas vulgaris 66/24; Proteus marg. 66/68; Proteus mirab. 564; Proteus mirab. 250; Serrata marcescens 67/14; Salmonella 29582; Salmonella gr. B; Providencia 70/13.

In said tests, the compounds of Examples 1 and 2 exhibited a higher inhibiting action at lower concentrations than p-aminomethyl-benzene-sulfonamide on the growth of the germ colonies.

The Pseudomonas, Staphylococcus and E. coli species were found to be particularly susceptible to the action of the products of Examples 1 and 2.

B. Protective action on experimentally induced burns

Experimental burns were produced on the back of male Sprague-Dawley rats, 24 hrs prior to depilation, by means of a hot-water apparatus capable of producing local burns of standard intensity. The seriousness of the lesion thus induced is evaluated by means of the intravenous injection of Evans Blue, a vital dye.

It was found from such tests that prior local administration of the products of Examples 1 and 2 at a dosage of 500 mg/kg exerts a protective action against experimentally induced burns, by inhibiting or decreasing the intensity and the seriousness of the local lesions. The protection exerted by the products of Examples 1 and 2 is superior to that exerted by p-aminomethyl-benzene-sulfonamide. The percent death rate obtained in the case of the burnt animals, after 48 hrs, is lower in the group of aminals treated with the products of Examples 1 and 2 than in the group of reference animals or in the group of animals treated with equivalent dosages of p-aminomethyl-benzene-sulfonamide.

C. Action on cicatrization

To evaluate the healing action of the products of Examples 1 and 2 holes of equal diameter were punctured through the ears of New Zealand rabbits, after which the time required for cicatrization of said holes to occur was determined in untreated reference rabbits, in rabbits treated locally around the hole punctured through the ear with a 10% p-aminomethyl-benzene-sulfonamide suspension or with a suspension of identical concentration of the products of Examples 1 and 2.

It was found that the tissue regeneration and cicatrization in the rabbits treated with the products of Examples 1 and 2 is much more rapid than in the reference animals or in the animals treated with p-aminomethyl-benzene-sulfonamide.

The therapeutic compositions of this invention are therapeutically useful in human medicine for their anti-bacterial chemotherapeutic activity and for their healing and protective action on burns.

The tests conducted show that the new compounds of this invention may be used more advantageously than p-aminomethyl-benzene-sulfonamide for the treatment of human patients, in all skin conditions susceptible to the action of sulfa-drugs.

The new compounds are topically administrable on the skin, as aerosols for local application, or formulated as ointments, creams, lotions or sprays.

They may be combined with suitable carriers or excipients. Non-limiting Examples of pharmacological formulations are given below:

Ointment, lotion, cream, spray, containing 0.5–2% active ingredient in combination with a suitable pharmaceutically acceptable carrier or excipient.

The daily administrable dosages vary according to the therapeutic requirements.

Having now described my invention what I claim as new and desire to secure by Letters Patent is:

1. p-Aminomethyl-benzene-sulfonamide derivatives having the formula:

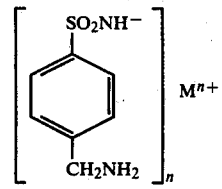

in which M is an ion of a metal atom selected from silver, zinc, aluminum, copper and cerium, and n is an integer from 1 to 4 and is equal to the valence of the metal ion M.

2. Therapeutic composition having in particular an anti-bacterial activity, and a healing and protective action on skin burns, comprising, as active ingredient, an effective amount of a p-aminomethyl-benzene-sulfonamide derivative having the formula:

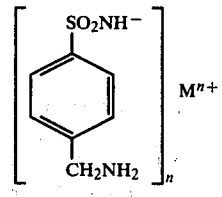

in which M is an ion of a metal atom selected from silver, zinc, aluminum, copper and cerium, and n is an integer from 1 to 4 and is equal to the valence of the metal ion M, together with suitable pharmaceutically acceptable carriers and excipients for topical cutaneous administration.

* * * * *